United States Patent [19]

Anderson

[11] 4,268,667

[45] May 19, 1981

[54] DERIVATIVES OF ARYL KETONES BASED ON 9,10-DIHYDRO-9,10-ETHANOANTHRACENE AND P-DIALKYL-AMINOARYL ALDEHYDES AS VISIBLE SENSITIZERS FOR PHOTOPOLYMERIZABLE COMPOSITIONS

[75] Inventor: Albert G. Anderson, Wilmington, Del.

[73] Assignee: E. I. Du Pont De Nemours and Company, Wilmington, Del.

[21] Appl. No.: 142,173

[22] Filed: Apr. 21, 1980

[51] Int. Cl.³ .................. C07D 241/04; G03C 1/68
[52] U.S. Cl. .................. 542/402; 252/426; 430/281; 430/917; 430/919; 430/923; 542/439; 564/426
[58] Field of Search ............ 260/576; 252/426; 542/402, 439; 430/281, 917, 919, 923

[56] References Cited

U.S. PATENT DOCUMENTS

| | | | |
|---|---|---|---|
| 2,406,645 | 8/1946 | Thomas | 260/671 |
| 3,373,075 | 3/1965 | Fekete et al. | 161/185 |
| 3,443,950 | 5/1969 | Rowlines | 96/87 |
| 3,479,185 | 11/1969 | Chambers | 96/84 |
| 3,549,367 | 12/1970 | Chang et al. | 96/35.1 |
| 3,637,618 | 1/1972 | May | 260/837 R |
| 3,652,275 | 3/1972 | Baum et al. | 204/159.14 |
| 3,661,576 | 5/1972 | Crary | 96/35.1 |
| 3,756,827 | 9/1973 | Chang | 96/86 P |
| 4,142,194 | 2/1979 | Hamlin | 354/318 |
| 4,162,162 | 7/1979 | Dueber | 96/35.1 |

FOREIGN PATENT DOCUMENTS

| | | |
|---|---|---|
| 1366769 | 9/1974 | United Kingdom . |
| 1453681 | 10/1976 | United Kingdom . |
| 1547548 | 6/1979 | United Kingdom . |

*Primary Examiner*—Jack P. Brammer
*Attorney, Agent, or Firm*—James A. Costello

[57] ABSTRACT

Compositions useful as visible sensitizers for photopolymerizable compositions, the sensitizers being α, β-unsaturated ketones formed by condensing the acetyl or diacetyl derivative of 9,10-dihydro-9,10-ethano(or propano)anthracene with a p-dialkylaminobenzaldehyde; and the photopolymerizable compositions comprising monomer, sensitizer, and initiator, with or without a binder.

12 Claims, No Drawings

DERIVATIVES OF ARYL KETONES BASED ON 9,10-DIHYDRO-9,10-ETHANOANTHRACENE AND P-DIALKYL-AMINOARYL ALDEHYDES AS VISIBLE SENSITIZERS FOR PHOTOPOLYMERIZABLE COMPOSITIONS

BACKGROUND OF THE INVENTION

1. Field of the Invention

Sensitizers for photopolymerizable compositions, the sensitizers being $\alpha,\beta$-unsaturated ketones based on 9,10-dihydro-9,10-ethano(or propano)-anthracene; and the photopolymerizable compositions comprising said sensitizers.

2. Description of the Prior Art

Use of sensitizers to extend the photosensitivity of photopolymerizable compositions into the visible region of the spectrum and to increase the speed of polymerization is known. Baum et al., U.S. Pat. No. 3,652,275, disclose selected bis(p-dialkylaminobenzylidene) ketones as sensitizers to enhance the efficiency of hexaarylbiimidazole initiator systems in photopolymerizable compositions.

Dueber, U.S. Pat. No. 4,162,162 discloses photopolymerizable compositions comprising a photopolymerizable monomer, an initiator, e.g., a hexaarylbiimidazole, and a sensitizing amount of a selected compound derived from aryl ketones and p-dialkylaminoaryl aldehydes.

Neither U.S. Pat. No. 3,652,275 nor U.S. Pat. No. 4,162,162 suggests the sensitizers of this invention, the most preferred of which are derived from 9,10-dihydro-9,10-ethanoanthracene disclosed in U.S. Pat. No. 2,406,645 (Thomas).

SUMMARY OF THE INVENTION

The ketone sensitizers of this invention have the formula:

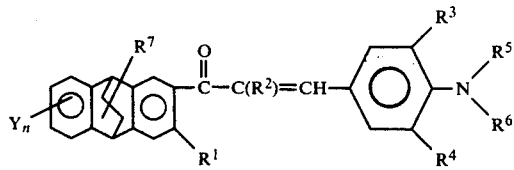

wherein:

Y is

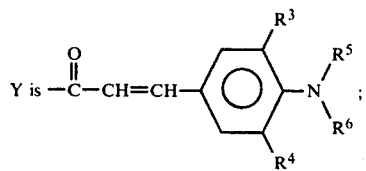

$R^1$ and $R^2$ are each H, or, $R^1 + R^2$ is —$CH_2$—;
$R^3$ is H, or, $R^3 + R^5$ is selected from —$CH_2CH_2$— and —$CH_2CH_2CH_2$—;
$R^4$ is H, or $R^4 + R^6$ is selected from —$CH_2CH_2$— and —$CH_2CH_2CH_2$—;
$R^5$ and $R^6$ are alkyl groups of 1 to 5 carbon atoms, or together are selected from —$(CH_2)_4$— and —$CH_2CH_2OCH_2CH_2$—;
$R^7$ is H or $CH_3$; and n is 0 or 1, with the proviso that when n is 1, $R^1$ and $R^2$ are H.

Preferred sensitizer compositions are those wherein $R^1$, $R^2$ and $R^7$ are H and n is 0. Most preferred are compositions where $R^1$, $R^2$, $R^4$ and $R^7$ are H, $R^5$ and $R^6$ are each $CH_3$ or $C_2H_5$, or $R^3 + R^5$ is —$CH_2CH_2CH_2$—, and n is 0. Preference is based on ease of preparation and sensitizer photospeeds.

The invention also concerns photopolymerizable compositions containing the sensitizers of formula I; the photopolymerizable compositions comprising a combination of:

(i) at least one nongaseous ethylenically unsaturated compound capable of forming a high molecular weight polymer by photoinitiated addition polymerization;

(ii) at least one 2,4,5-triarylimidazolyl dimer initiator consisting of two 2,4,5-triarylimidazolyl radicals bound together by a single covalent bond; and (iii) at least one $\alpha,\beta$-unsaturated ketone sensitizer of formula I.

For practical considerations, it is preferred to employ a compound (i) which has a boiling point above 100° C. at normal atmospheric pressure.

The photopolymerizable compositions can contain a polymeric binder to improve strength or to improve or effect adherence to a substrate. The relative concentrations of elements (i), (ii), and (iii), and the binder are as follows. The ethylenically unsaturated compound, (i), is present in an amount of about 3 to 100 parts per 100 parts of the combined weight of (i) and binder; the binder being present in an amount of 0 to about 97 parts per 100 parts of their combined weight. The initiator, (ii), is present in an amount of about 0.01 to 20 parts per 100 parts of the combined weight of (i) and binder. The sensitizer, (iii), is present in an amount of about 0.001 to 15 parts per 100 parts of the combined weight of (i) and binder, more preferably at about 1.0 to 10 parts per 100 parts.

The photopolymerizable compositions of this invention can contain other additives in addition to binders. The types and amounts of such additives will be obvious to those skilled in the art. Several types of additives will be described hereafter.

DETAILS OF THE INVENTION

Preparation of Sensitizers

The sensitizers of this invention are prepared by reacting the known 9,10-dihydro-9,10-ethanoanthracene or 9,10-dihydro-9,10-propanoanthracene with acetyl chloride or acetic anhydride in the presence of aluminum chloride to obtain as an intermediate the corresponding 2-acetyl or 2,6(7)-diacetyl derivative shown by formula B. With an excess of acylating agent, a mixture of the 2,6- and 2,7-diacetyl derivatives is usually obtained. A typical reaction sequence for preparing the intermediate, B, is given as follows:

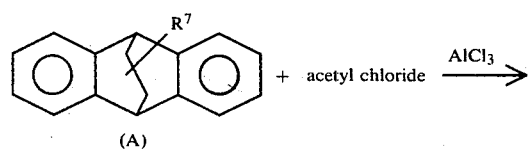

(A)

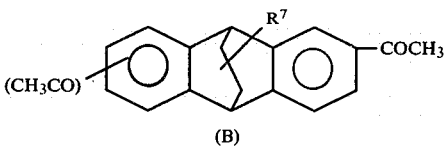

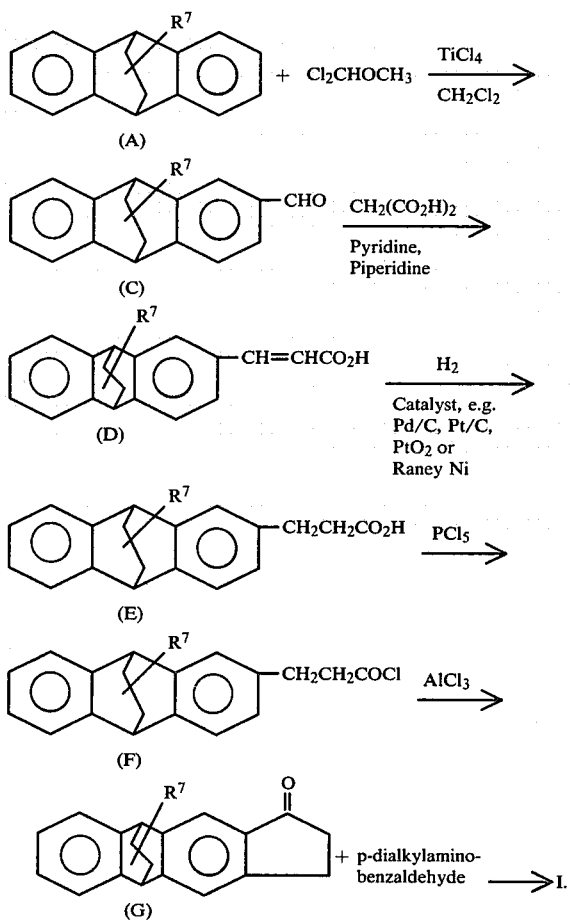

Condensation of the intermediate acetyl compounds with a p-dialkylaminobenzaldehyde in the presence of a base, e.g., sodium hydroxide, gives the $\alpha,\beta$-unsaturated ketones, I, of the invention.

Sensitizers of this invention wherein $R^1+R^2$ is $-CH_2-$ can be prepared, for example, by the following reaction sequence:

In the reaction sequences depicted above, carbonylation of the starting hydrocarbon with 1,1-dichloromethyl methyl ether in the presence of TiCl$_4$ gives the corresponding aldehyde C. Condensation of C with malonic acid in the well-known Perkin or related condensation reaction can give D, and catalytic hydrogenation of D can give the substituted propionic acid E. Conversion of E to the acid chloride with PCl$_5$ followed by intramolecular Friedel-Crafts cyclization can give the cyclic ketones G. Intramolecular Friedel-Crafts cyclization is described by Johnson in Organic Reactions, Volume II, John Wiley & Sons, Inc., New York, pages 130 to 156.

Photopolymerizable Compositions

The Ethylenically Unsaturated Compound (i)

Contemplated monomers include those which form both water-soluble and water-insoluble polymers. Typical monomers are alkylene or polyalkylene glycol diacrylate prepared from an alkylene glycol of 2 to 15 carbons or a polyalkylene ether glycol of 1 to 10 ether linkages, and those disclosed in Martin and Barney, U.S. Pat. No. 2,927,022, e.g., those having a plurality of addition polymerizable ethylenic linkages, particularly when present as terminal linkages, and especially those wherein at least one and preferably most of such linkages are conjugated with a doubly bonded carbon, including carbon doubly bonded to carbon and to such heteroatoms as nitrogen, oxygen and sulfur. Outstanding are such materials wherein the ethylenically unsaturated groups, especially the vinylidene groups, are conjugated with ester or amide structures.

The following specific compounds are illustrative of this class: unsaturated esters of alcohols, preferably polyols and particularly such of the alphamethylene carboxylic acids, e.g., ethylene glycol diacrylate, diethylene glycol diacrylate, glycerol diacrylate, glycerol triacrylate, ethylene glycol dimethacrylate, 1,3-propanediol dimethacrylate, 1,2,4-butanetriol trimethacrylate, 1,4-cyclohexanediol diacrylate, 1,4-benzenediol dimethacrylate, pentaerythritol tetramethacrylate, 1,3-propanediol diacrylate, 1,3-pentanediol dimethacrylate, the bis-acrylates and methacrylates of polyethylene glycols of molecular weight 200–500, and the like; unsaturated amides, particularly those of the alphamethylene carboxylic acids, and especially those of alpha-omega-diamines and oxygen-interrupted omega-diamines, such as methylene bis-acrylamide, methylene bis-methacrylamide, ethylene bis-methacrylamide, 1,6-hexamethylene bis-acrylamide, diethylene triamine tris-methacrylamide, bis(gamma-methacrylamidopropoxy) ethane beta-methacrylamidoethyl methacrylate, N-(beta-hydroxyethyl)-beta-(methacrylamido) ethyl acrylate and N,N-bis(beta-methacryloxyethyl) acrylamide; vinyl esters such as divinyl succinate, divinyl adipate, divinyl phthalate, divinyl terephthalate, divinyl benzene-1,3-disulfonate, and divinyl butane-1,4-disulfonate, styrene and derivatives thereof and unsaturated aldehydes, such as sorbaldehyde (hexadienal).

An outstanding class of these preferred addition polymerizable components are the esters and amides of alpha-methylene carboxylic acids and substituted carboxylic acids with polyols and polyamines wherein the molecular chain between the hydroxyls and amino groups is solely carbon or oxygen-interrupted carbon. The preferred monomeric compounds are polyfunctional, but monofunctional monomers can also be used. In addition, the polymerizable, ethylenically unsaturated polymers of Burg U.S. Pat. No. 3,043,805, Martin U.S. Pat. No. 2,929,710 and similar materials may be used alone or mixed with other materials. Acrylic and methacrylic esters of polyhydroxy compounds such as pentaerythritol and trimethylolpropane, and acrylic and methacrylic esters of adducts of ethylene oxide and polyhydroxy compounds such as those described in Cohen and Schoenthaler, U.S. Pat. No. 3,380,831 are also useful. The photocrosslinkable polymers disclosed in Schoenthaler, U.S. Pat. No. 3,418,295, and Celeste, U.S. Pat. No. 3,448,089, may also be used. The amount of monomer added varies with the particular polymer used. Other useful ethylenically unsaturated compounds are the ethylenically unsaturated diester polyhydroxy polyethers described in U.S. Pat. Nos. 3,661,576, 3,373,075 and 3,637,618.

Many ethylenically unsaturated monomers are subject to thermal polymerization, especially when stored for long periods or at elevated temperatures. When such compounds are supplied commercially, it is customary for them to contain a small amount of a thermal polymerization inhibitor. These inhibitors can be left in the monomers when the photopolymerizable compositions of this invention are prepared, as was done in the Examples which follow. The resulting compositions usually have satisfactory thermal stability. If unusual thermal exposure is anticipated, or if monomers containing little or no thermal polymerization inhibitor are employed, compositions with adequate shelf life can be obtained by incorporating about 1 to 500 ppm by weight of monomer, of a thermal polymerization inhibitor such as hydroquinone, methylhydroquinone, p-methoxyphenol, and the nitroso dimer inhibitor systems described in Pazos, U.S. Pat. No. 4,168,982.

The Initiator (ii)

Dimers consisting of two 2,4,5-triarylimidazolyl radicals bound together by a single covalent bond are especially preferred initiators. Such dimers are photodissociable to the corresponding triarylimidazolyl radicals. The dimers absorb maximally in the 255 to 275 nm region, and usually show some lesser absorption in the 300 to 375 nm region. Although the absorption bands tend to tail out to include wavelengths as high as about 430 nm, they normally require radiation rich in the 255 to 375 nm region for their dissociation.

Suitable 2,4,5-triarylimidazolyl dimers include 2-(o-chlorophenyl)-4,5-diphenylimidazolyl dimer, 2-(o-chlorophenyl)-4,5-di(m-methoxyphenyl)imidazolyl dimer, 2-(o-fluorophenyl)-4,5-diphenylimidazolyl dimer, 2-(o-methoxyphenyl)-4,5-diphenylimidazolyl dimer, 2-(p-methoxyphenyl)-4,5-diphenylimidazolyl dimer, 2,4-di(p-methoxyphenyl)-5-phenylimidazolyl dimer, 2-(2,4-dimethoxyphenyl)-4,5-diphenylimidazolyl dimer, 2-(p-methylmercaptophenyl)-4,5-diphenylimidazolyl dimer, and the like. Other suitable dimers are disclosed by Baum and Henry in U.S. Pat. No. 3,652,275, column 5, line 44, to column 7, line 16, the disclosure of which is incorporated herein by reference.

The imidazolyl dimers can be used with a free-radical producing hydrogen or electron donor such as 2-mercaptobenzoxazole, 2-mercaptobenzthiazole, Leuco Crystal Violet or tris(4-diethylamino-2-methylphenyl)-methane. Other leuco dyes, e.g., those disclosed in U.S. Pat. No. 3,652,275, column 7, line 24, to column 11, line 32, can also be used. By the term "leuco dye" is meant the colorless, i.e., reduced, form of a dye compound which can be oxidized to its colored form by the triarylimidazolyl radical.

The Sensitizer (iii)

The α,β-unsaturated ketone sensitizers of this invention, described broadly above, have been found to absorb radiation in the broad spectral range of about 300 to 700 nm. The maximum absorption ($\lambda_{max}$) is in the range of about 350 to 550 nm and preferably about 400 to 500 nm.

Other Additives

It is preferred that the photopolymerizable compositions contain a polymeric binder which can serve to strengthen the composition or adhere it to a substrate. Radiation-transparent and film-forming polymer binders are preferred. Examples of suitable binders are thermoplastic macromolecular organic polymers which have number average molecular weights of at least about 1500, preferably at least about 4000, including such polymer types as: (a) copolyesters based on terephthalic, isophthalic, sebacic, adipic and hexahydroterephthalic acids; (b) nylons or polyamides; (c) vinylidene chloride copolymers; (d) ethylene/vinyl acetate copolymers; (e) cellulosic ethers; (f) synthetic rubbers; (g) cellulose esters; (h) polyvinyl esters including polyvinyl acetate/acrylate and polyvinyl acetate/-methacrylate copolymers; (i) polyacrylate and α-alkylpolyacrylate esters, e.g., polymethyl methacrylate, polyethyl methacrylate, and methyl methacrylate/ethyl acrylate copolymers; (j) high molecular weight polyethylene oxides of polyglycols having average molecular weights of about 4000 to 1,000,000; (k) polyvinyl chloride and copolymers; (l) polyvinyl acetal; (m) polyurethanes; (n) polycarbonates; (o) polystyrenes.

In a particularly preferred embodiment of the invention, the polymeric binder is selected so that the unexposed photopolymerizable coating is soluble in predominantly aqueous solution, for example dilute aqueous alkaline solution, but upon exposure to actinic radiation becomes relatively insoluble therein. Typically, polymers which satisfy these requirements are carboxylated polymers such as vinyl addition polymers containing free carboxylic acid groups. A most preferred group of binders includes polyacrylate esters and poly-α-alkylacrylate esters which contain carboxyl groups; particularly preferred are the polymethyl methacrylate esters.

In preferred positive-working photopolymerizable compositions, nitroaromatic photoinhibitors as disclosed in British Pat. No. 1,547,548 are present. These compounds are used in amounts of about 0.5 to 15 parts by weight per 100 parts of the combined weight of ethylenically unsaturated compound and binder.

A wide range of nonpolymerizable plasticizers are effective in achieving improved exposure and development temperature latitude. When a macromolecular binder is present in the layer, plasticizer would be selected which is compatible with the binder as well as the ethylenically unsaturated monomer and other components of the composition. With acrylic binders, for example, plasticizers can include dibutyl phthalate and other esters of aromatic acids; esters of aliphatic polyacids such as diisooctyl adipate, and nitrate esters; aromatic or aliphatic acid esters of glycols, polyoxyalkylene glycols, aliphatic polyols; alkyl and aryl phosphates; low molecular weight polyesters of poly-α-methylstyrenes; chlorinated paraffins; and sulfonamide types can be used. In general, water insoluble plasticizers are preferred for greater high humidity storage stability, but are not necessary to get improved latitude. Other inert additives can be employed such as dyes, pigments and fillers. These additives are generally present in minor amounts so as not to interfere with the exposure of the photopolymerizable layer.

Substrates for the Photopolymerizable Compositions

The photopolymerizable compositions can be coated on a wide variety of substrates. By "substrate" is meant any natural or synthetic support, preferably one which is capable of existing in a flexible or rigid film or sheet form. For example, the substrate can be a metal sheet or foil, a sheet or film of synthetic organic resin, cellulose paper, fiberboard, and the like, or a composite of two or more of these materials.

The particular substrate will generally be determined by the use application involved. For example, when printed circuits are produced, the substrate may be a plate which is a copper coating on fiberboard; in the preparation of lithographic printing plates, the substrate is anodized aluminum. Specific substrates include alumina-blasted aluminum, anodized aluminum, alumina-blasted polythylene terephthalate film, polyethylene terephthalate film, e.g., resin-subbed polyethylene therephthalate film, polyvinyl alcohol-coated paper, crosslinked polyester-coated paper, nylon, glass, cellulose acetate film, heavy paper such as lithographic paper, and the like.

An antihalation material can be used beneath the photopolymerizable layer, for example, in the substrate or on its surface. When an antihalation layer is used between the photopolymerizable layer and the substrate, the layer must have adequate adhesion to the substrate and the photopolymerizable layer and not react with the radiation-adsorptive material. Antihalation pigments and resin carriers are described in British Pat. No. 1,366,769.

The photopolymerizable composition is usually applied to the substrate as a solution or dispersion in a carrier solvent. The solution or dispersion can be sprayed, brushed, applied by a roller or an immersion coater, flowed over the surface, picked up by immersion or applied to the substrate by other suitable means. The solvent is then allowed to evaporate. In general, solvents are employed which are volatile at ordinary pressures. Examples of suitable solvents include water; amides such as N,N-dimethylformamide and N,N-dimethylacetamide; alcohols and ether alcohols such as methanol, ethanol, 1-propanol, 2-propanol, butanol, ethylene glycol, 2-butoxyethanol, and 2-ethoxyethanol; esters such as methyl acetate and ethyl acetate; aromatic hydrocarbons and aromatic halocarbons such as benzene, o-dichlorobenzene and toluene; ketones such as acetone, 2-butanone, and 3-pentanone; aliphatic halocarbons such as 1,1,1-trichloroethane, methylene chloride, chloroform, 1,1,2-trichloroethane, 1,1,2,2-tetrachloroethane, 1,1,2-trichloroethylene; miscellaneous solvents such as dimethyl sulfoxide, pyridine, tetrahydrofuran, 1,2-dimethoxyethene, dioxane, dicyanocyclobutane, N-methylpyrrolidone; and mixtures of these solvents in various proportions as may be required to attain solutions. Alternatively, the photopolymerizable composition can be formed into a film and the film can be applied to the substrate.

Preferably the layers of the photopolymerizable compositions have a thickness ranging from about 0.0001 inch ($\sim$2.5 $\mu$m) to 0.01 inch ($\sim$250 $\mu$m) and are applied to a thin, flexible, polymeric film support which can transmit actinic radiation to the photopolymerizable layer. The opposite side of the photopolymerizable layer can have adhered thereto a protective cover layer or cover sheet wherein the sheet has less adhesion to the layer than to the film support. A particularly preferred support is a transparent polyethylene terephthalate film having a thickness of about 0.001 inch ($\sim$25 $\mu$m). Polyethylene, 0.001 inch ($\sim$25 $\mu$m) is a preferred cover sheet; polyvinyl alcohol coating is a preferred cover layer.

Any convenient source of actinic radiation providing wavelengths in the region of the spectrum that overlap the $\alpha,\beta$-unsaturated ketone sensitizers absorption bands can be used to activate the photopolymerizable compositions for triarylimidazolyl radical formation, image formation and photopolymerization initiation. The radiation can be natural or artificial, monochromatic or polychromatic, incoherent or coherent, and for high efficiency should correspond closely in wavelengths to the sensitizer's principal absorption bands and should be sufficiently intense to activate a substantial proportion of the sensitizer.

Conventional radiation sources include fluoroescent lamps, mercury, metal additive and arc lamps providing narrow or broad radiation bands centered near 405, 436 and 546 nm (Hg) wavelengths. Coherent radiation sources are the pulsed xenon, argon ion and/or ionized neon-lasers whose emulsions fall within or overlap the visible absorption bands of the sensitizer. Ultraviolet and visible emitting cathode ray tubes widely useful in printout systems for writing on photosensitive materials are also useful with the subject compositions. These cathode ray tubes comprise an ultraviolet or visible-emitting phosphor internal coating as the means for converting electrical energy to light energy and a fiber optic face plate as the means for directing the radiation to the photosensitive target. Electron accelerators and electron beam sources through an appropriate mask are also suitable.

The radiation exposure times can vary from fractions of a second to minutes, depending upon the intensity and spectral energy distribution of the radiation used, its distance from the photopolymerizable layer, and the nature and amounts of the unsaturated compounds in the layer. Customarily, a distance of about 1.5 to 60 inches (3.8 to 153 cm) from the photopolymerizable layer is used. Exposure temperatures are not particularly critical, but it is preferred to operate at about ambient temperatures or slightly higher, i.e., about 20° to 50° C.

Imagewise exposure is conveniently carried out by exposing the photopolymerizable element to actinic radiation through a process transparency, that is, an image-bearing transparency consisting of areas substantially opaque and substantially transparent to the radiation being used, where the opaque areas can be substantially of the same optical density; for example, a so-called line or halftone negative or positive. Suitable process transparencies also include those with a graded range of opaque areas; for example, a continuous tone negative. Process transparencies can be constructed of any suitable materials including cellulose acetate film and polyester film.

After exposure, the image is developed. Development can be by toning, i.e., dusting with a fine pigment which selectively adheres to the tacky unhardened areas, by dye imbibition or by modulation of diffusion. Generally, however, the portions of the layer corresponding to the unexposed portions are removed, e.g., in lithographic applications. This method of development can be achieved by pressure transfer, differential adhesion of the exposed versus unexposed areas, use of peel apart transfer, and, preferably, by solvent washout. The solvent liquid used for development should have good solvent action on the nonpolymerized portions of the composition, and little action on the insolubilized image in the time required to remove the soluble portions.

Utility

The photopolymerizable compositions of this invention have very little residual color and good solubility and shelf life; they are useful in printing plates for offset and letter press, engineering drafting films, as well as photoresists in making printed circuits or in chemical milling, and as solder masks. In printing plate applications, an important use is in a positive/negative two-exposure imaging system of a positive photopolymer litho printing plate. The compositions are also useful in positive working photopolymer litho films. Still other uses are for preparing colored images from color separation negatives suitable for color-proofing. The images formed with these elements can be used for making copies by thermal transfer to a substrate. Other specific uses will be evident to those skilled in the art.

In photoresist applications, thin film resists prepared from the composition are useful in the preparation of microcircuits. The resists can be either solvent soluble or aqueous developable. Solder masks are protective coatings which are selectively applied to portions of a printed circuit board surface to confine solder to pad areas on the board and to prevent bridging between conductors during tinning operations and during soldering of components. A solder mask also functions to prevent or minimize corrosion of the base copper conductors and as a dielectric to insulate certain components for adjacent circuitry.

Photopolymerizable compositions containing the $\alpha,\beta$-unsaturated ketone sensitizers of this invention show good visible light sensitization. The increase in speed results in a saving of energy and costs related thereto since lower energy exposure sources can be used in exposure of the photopolymerizable element or more elements can be exposed and developed in a given amount of time. Alternatively, the photopolymerizable layer can be exposed by means of an exposure source maintained at a greater distance than normal for known sensitized elements. This permits the exposing radiation to be collimated which is of particular advantage in forming halftone dots having substantially perpendicular sides. The broad sensitization range coupled with the effectiveness of sensitization enables useful positive polymeric images to be formed by a double exposure process, first, imagewise in the ultraviolet region of the spectrum and then overall in the visible region of the spectrum utilizing specific nitroaromatic photoinhibitors.

The following Examples illustrate the invention, Examples 6 to 11 representing preferred embodiments. All parts and percentages are by weight and all degrees and Celcius unless otherwise stated.

Preparation of Intermediates

The reactant, 2-acetyl-9,10-dihydro-9,10-ethanoanthracene, was prepared by the following procedure. To a stirred solution of 100 g (0.485 M) of 9,10-dihydro-9,10-ethanoanthracene and 50 g (0.49 M) of acetic anhydride in 500 ml of dichloroethane was added 135 g (1.01 M) of aluminum chloride in portions at 0° to 10° over a 1.5-hour period. The pale brown mixture was stirred at room temperature overnight and decomposed by successive addition of 500 ml of water and 100 ml of 6 N HCl. The organic layer was separated and the aqueous layer was extracted twice with $CH_2Cl_2$; washed with brine, dried and evaporated. The residual viscous oil was crystallized from hexane to give 100.8 g (84.4%) of 2-acetyl-9,10-dihydro-9,10-ethanoanthracene. M.p., 91° to 92°; Pmr ($CDCl_3$) δ 1.67 (t, 4H, bridge), 2.52 (s, 3H, $CH_3$), 4.37 (s, 2H, bridge head), 6.95-7.35 (m, 5H), 7.60-7.90 (dxd and d, 2H).

The reactant, 2,6(7)-diacetyl-9,10-dihydro-9,10-ethanoanthracene, was prepared as follows. To a gray suspension of 100 g (0.75 M) of $AlCl_3$ in 125 ml of dichloroethane was added 35 ml (0.37 M) of acetic anhydride at 20° to 25° over 1 hour. A solution of 21 g (0.10 M) of 9,10-dihydro-9,10-ethanoanthracene in 125 ml of dichloroethane was added at 20° over a 30 minute period. The dark brown suspension was stirred at room temperature overnight, heated to distill about 125 ml of the solvent, cooled, and poured into ice water containing 80 ml of concentrated HCl. The organic layer was separated and the aqueous layer was extracted with $CH_2Cl_2$ twice. The combined organic extracts were washed with saturated sodium chloride solution, dried and evaporated. A toluene solution of the dark residual oil was treated with charcoal, filtered, evaporated, and the residue was vacuum distilled by a bulb-to-bulb distillation from a 200° air bath to give 18.0 g (62%) of a mixture of 2,6(7)-di-acetyl-9,10-dihydro-9,10-ethanoanthracene as an amber glass. The pmr in $CDCl_3$ showed excess acetyl group. Pmr in $CDCl_3$: 1.65 (s, 4.1H, bridge), 2.50 (s, 6.9H, $CH_3$), 4.45 (s, 2.0 H, bridgehead), 7.30 (d J≈8 Hz, 2.3 H, arom), 7.73 (d x d J≈8, 1.5 Hz, 2.0 H, arom), 7.90 (d J≈1.5 Hz, 2.0 H, arom).

EXAMPLE 1

3-[4-Dimethylamino)phenyl]-1-(9,10-dihydro-9,10-ethanoanthracen-2-yl)-2-propen-1-one (2)

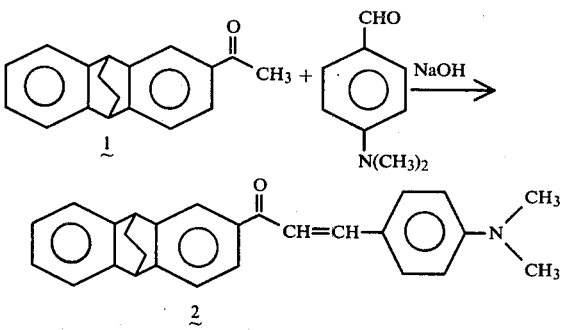

A solution of 2.3 g of p-dimethylaminobenzaldehyde (15 mmole), 3.7 g of 2-acetyl-9,10-dihydro-9,10-ethanoanthracene (1) (15 mmole) and 0.66 g of sodium hydroxide (16.5 mmole) in 100 ml of ethanol was stirred under nitrogen at 40° to 45° for 18 hr. A yellow solid precipitated which was separated by filtration and recrystallized from 300 ml of ethanol to give 1.1 g of the product 2, 3-[4-(dimethylamino)phenyl]-1-(9,10-dihydro-9,10-ethanoanthracen-2-yl)-2-propen-1-one. Partial evaporation of the filtrate and addition of water to a final volume of about 100 ml (25% water) gave, on cooling, an additional 2.1 g of product. On standing, an additional 1.0 g of 2 was precipitated from the reaction mixture: total yield, 4.2 g (74%). Mp 184° to 186°. $\lambda_{max}$ ($C_2H_5OH$): 418 nm ($\epsilon$=33,500), 270 mn (15,200). Calcd for $C_{27}H_{25}NO$: C, 85.45; H, 6.64; N, 3.69. Found: C, 85.06, 84.91; H, 6.89, 6.92; N, 3.66, 3.65.

EXAMPLE 2

3-[4-(Diethylamino)phenyl]-1-(9,10-dihydro-9,10-ethanoanthracen-2-yl)-2-propen-1-one (3)

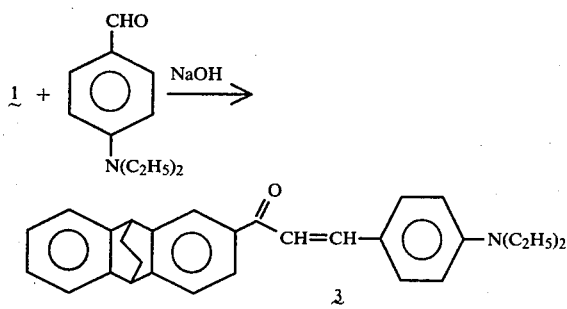

A solution of 14.3 g of p-diethylaminobenzaldehyde (0.0805 M), 20.0 g of 1 (0.0805 M) and 3.6 g of sodium hydroxide (0.090 M) in 400 ml of ethanol was stirred under nitrogen at about 62° for 48 hr. The reaction mixture was cooled to 0° and the precipitated solid product was separated by filtration and washed with cold ethanol to give 17.6 g (54% yield) of the product 3, 3-[4-(diethylamino)phenyl]-1-(9,10-dihydro-9,10-ethanoanthracen-2-yl)-2-propen-1-one. The filtrate was evaporated and the residue taken up in ether and water. The organic layer was washed with water, dried, and evaporated to give a red oil which was dissolved in ether and the solution was passed through a column of neutral alumina. The ether was evaporated and the residue dissolved in 100 ml of hot ethanol. Slow cooling of this solution until precipitation occurred followed by cooling in an ice bath yielded an additional 7.6 g (23% yield) of 3.

A sample of product prepared on a 0.015 M scale was recrystallized from cyclohexane. Mp 100° to 101°. $\lambda_{max}$ (CHCl$_3$): 423 nm ($\epsilon$=27,700), 280 nm (16,900). Calcd for C$_{29}$H$_{29}$NO: C, 85.46; H, 7.17; N, 3.44. Found: C, 85.11; H, 7.10; N, 3.21.

EXAMPLE 3

1-(9,10-Dihydro-9,10-ethanoanthracen-2-yl)-3-(1,2,6,7-tetrahydro-3H,5H-benzo[i,j]quinolizin-9-yl)-2-propen-1-one (4)

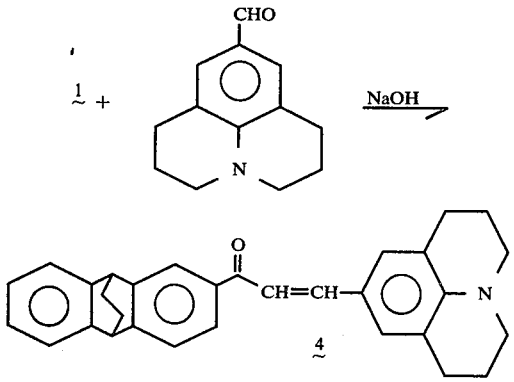

A solution of 3.0 g of 9-formyl-1,2,6,7-tetrahydro-3H,5H-benzo[i,j]quinoline (15 mmole), 3.7 g of 1 (15 mmole) and 0.66 g of sodium hydroxide (16.5 mmole) in 75 ml of ethanol was stirred under nitrogen at about 60° for 30 hr. After the reaction mixture stood at room temperature for 64 hr, a red solid separated which was isolated by pouring off the supernatant liquid. The solid was dissolved in boiling cyclohexane, and the solution was filtered to remove a small amount of dark solid. After cooling, 1.4 g (22%) of orange solid 1-(9,10-dihydro-9,10-ethanoanthracen-2-yl)-3-(1,2,6,7-tetrahydro-3H,5H-benzo[i,j]quinolizin-9-yl)-2-propen-1-one was obtained. Mp 103° to 105° with some initial softening at 84° to 86°. $\lambda_{max}$ (CHCl$_3$): 440 nm ($\epsilon$=25,700), 363 nm (8,920), 274 nm (15,400). Calcd for C$_{31}$H$_{29}$NO: 86.27, H, 6.77; N, 3.24. Found: C, 84.43, 84.35; H, 6.69, 7.01; N, 3.20, 3.05.

Water and ether were added to the supernatant liquid and the organic layer was washed with water, dried and evaporated to give a dark oil. The oil was dissolved in boiling cyclohexane and filtered to remove some dark material. The filtrate was combined with the mother liquor of the previous recrystallization, evaporated to about 100 ml, and allowed to stand overnight. A dark oil separated. On cooling in ice the dark oil became solid and yellow crystals separated. The yellow crystals were filtered off and dried to give an additional 1.0 g of product. Evaporation of the mother liquor gave an additional 0.8 g. Total yield: 3.2 g (49%).

EXAMPLE 4

2,6(7)-Bis[p-(diethylamino)cinnamoyl]-9,10-dihydro-9,10-ethanoanthracene (6)

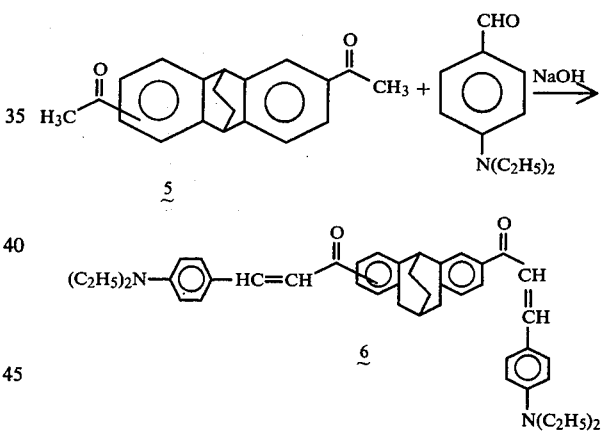

A solution of 1.77 g of p-diethylaminobenzaldehye (10 mmole), 1.45 g of a mixture of 2,6-diacetyl-9,10-dihydro-9,10-ethanoanthracene and 2,7-diacetyl-9,10-dihydro-9,10-ethanoanthracene (5) (5 mmole) and 0.22 g of sodium hydroxide (5.5 mmole) in 30 ml of ethanol was stirred under nitrogen at about 60° for 4 hr. Then the volume was increased to 50 ml by addition of ethanol, and the reaction mixture was heated at reflux for 18 hr. On cooling a dark yellow solid separated which was filtered off. Yield of condensation product, 6, was 0.70 g (23%). Melting range 170° to 175°. The filtrate was diluted with chloroform and the organic layer was washed with water. Evaporation gave a dark red oil which was chromatographed on silica gel. Elution with methylene chloride gave 0.6 g (20%) of a dark yellow-red solid. $\lambda_{max}$ (CHCl$_3$) 424 nm ($\epsilon$=33,400), 265 nm ($\epsilon$=36,200). Calcd for C$_{42}$H$_{49}$N$_2$O$_2$: C, 82.86; H, 7.28; N, 4.60. Found: C, 80.14, 80.76; H, 7.08, 6.93; N, 3.93, 3.85.

EXAMPLE 5

2,6(7)-Bis[p-(dimethylamino)cinnamoyl]-9,10-dihydro-9,10-ethanoanthracene (7)

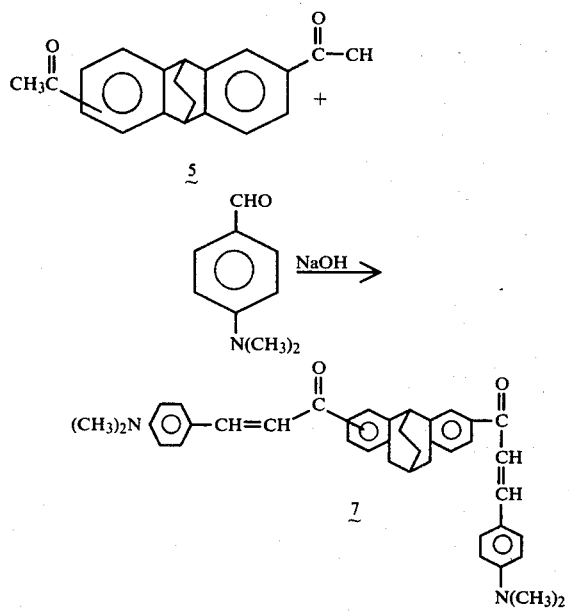

A solution of 0.745 g (5 mmole) of p-dimethylaminobenzaldehyde, 0.725 g (2.5 mmole) of a mixture of 2,6(7)-diacetyl-9,10-dihydro-9,10-ethanoanthracene (5), and 0.11 g (2.75 mmole) of sodium hydroxide in 30 ml of ethanol was heated and stirred at 60° under nitrogen for 65 hours. An additional 10 ml of ethanol was added and the reaction mixture was heated under reflux an additional 8 hr and then cooled slowly to 0°. The precipitated solid was separated, washed with ethanol, and dried to give 0.6 g (43% yield) of condensation product, 7. $\lambda_{max}$ (CHCl$_3$) 423 nm ($\epsilon$=29,200); 263 nm ($\epsilon$=32,200). Calcd for C$_{38}$H$_{36}$N$_2$O$_2$: C, 82.58; H, 6.57; N, 5.07. Found: C, 78.35, 78.38; H, 6.23, 6.18; N, 3.92, 4.03.

EXAMPLES 6 TO 11

The oriented polyester films employed as substrates in Examples 6 to 11 were 4-mil (102 μm) polyethylene terephthalate films which were sub-coated with a copolymer resin comprising a sequentially polymerized mixture of a vinylidene chloride/alkyl acrylate/itaconic acid copolymer and an alkyl acrylate polymer as described by Rawlins in U.S. Pat. No. 3,443,950. To the copolymer resin, before coating, was added a methyl methacrylate:ethyl acrylate:acrylic acid (37:56:7) terpolymer (molecular weight 260,000 and acid number 76–85), dispersed with ammonia. The coated films were stretched and a thin layer of the terpolymer in water was added onto the first sub-coating.

The radiation source used for the exposure of the photosensitive elements of these Examples was a 4 KW pulsed xenon arc (Macbeth) at a distance of 60 inches (152 cm).

The exposed elements were processed through an automatic processor in which the film is fed, image up, in a straight through path into a development section, then to a rinse section, and finally to a drier section, as described by Hamlin in U.S. Pat. No. 4,142,194, at rates as specified in each Example. Processing temperature was 22.2°, and the solvent was an aqueous solution of a mixture of potassium carbonate and potassium bicarbonate. The processed elements were rinsed with water in the rinse chamber at 32.2°.

EXAMPLE 6

The following photopolymerizable composition was prepared:

|  | Wt. Used (g) |
| --- | --- |
| Aqueous Component |  |
| Distilled water | 68.6 |
| Acrylic latex binder ("Acrysol" -94, Rohm & Haas Co.) | 34.8 |
| 40% Polyethylene wax dispersed in water ("Misco" AC-392, Misco Products Co., Wheeling, Illinois) | 10.0 |
| Octylphenoxy polyethoxyethanol dispersing agent, ("Triton" X-100, Rohm & Haas Co.), 10% solution | 3.0 |
| Zinc complex solution (ammonium carbonate, ammonia, zinc oxide, water solution; 7.2% zinc) | 3.1 |
| Organic Component |  |
| Tetraethylene glycol dimethacrylate | 1.7 |
| Trimethylolpropane triacrylate | 1.7 |
| Sensitizer from Example 2 | 0.1 |
| 6-Nitroveratraldehyde photoinhibitor | 0.56 |
| 2-(o-Chlorophenyl)-4,5-diphenylimidazolyl dimer | 0.6 |
| 2-(o-Chlorophenyl)-4,5-di(m-methoxyphenyl)-imidazolyl dimer | 0.6 |
| Methylene chloride | 8.5 |

Both components were combined and the mixture was emulsified for 5 minutes in a blender. To the emulsion was added 2 g of a 25% water solution of a fluorinated hydrocarbon surfactant having the following chemical structure: (C$_8$F$_{17}$SO$_2$N(C$_2$H$_5$)CH$_2$CO$_2$)$^\ominus$K$^\oplus$. The mixture was coated on the resin-subbed side of an oriented polyethylene terephthalate film substrate using a 2-mil (~51-μm) doctor knife. The coating was dried with a hot air gun. The dried film was heated at 95° to 100° for 5 minutes and an oriented polyethylene terephthalate film cover sheet was laminated thereon.

Portions of this photosensitive element were exposed to radiation for periods of 5 to 25 seconds through a process transparency in contact with the cover sheet. The process transparency was removed and the elements reexposed overall for 40 seconds to radiation through a cut-off filter which absorbed all radiation below 400 nm. The elements were processed through the automatic processor at a rate of 87 in/min (221 cm/min) to produce a good clean positive image.

EXAMPLE 7

The photopolymerizable composition of Example 6 was prepared except that the sensitizer from Example 2 was replaced with 0.22 g of the sensitizer from Example 3. A portion of the photosensitive element prepared from the emulsified composition was exposed to radiation for 10 seconds through a process transparency in contact with the cover sheet. The process transparency was removed and the element reexposed overall for 25 seconds to radiation through the cut-off filter. The element was processed through the automatic processor at a rate of 49 inches/min (124 cm/min) to produce a clear positive image with a low level of background.

EXAMPLE 8

The photopolymerizable composition of Example 6 was prepared except that the sensitizer from Example 2 was replaced with 0.20 g of the sensitizer from Example 1. A portion of the photosensitive element prepared from the emulsified composition was exposed to radiation for 10 seconds through a process transparency in contact with the cover sheet. The process transparency was removed and the element reexposed overall for 25 seconds to radiation through the cut-off filter. The element was processed through the automatic processor at a rate of 49 inches/min (124 cm/min) to produce a sharp positive image on an almost clear background.

EXAMPLES 9 TO 11

Photopolymerizable compositions were prepared as described in Examples 6 to 8 and photosensitive elements were prepared from each of these compositions. Portions of the photosensitive elements were exposed to radiation through the cut-off filter without a process transparency for a time sufficient to obtain a full density, shiny, image in each Example. The exposed elements were processed through the automatic processor at the maximum rate in which the unexposed composition was removed (clearing rate). Results are summarized in Table 1.

TABLE 1

| Example | Sensitizer from Example | Relative Photospeed |
|---------|-------------------------|---------------------|
| 9       | 2                       | 1.2                 |
| 10      | 3                       | 1.5                 |
| 11      | 1                       | 1.0                 |

EXAMPLE 12

The following stock solution was prepared:

| Component | Wt. (g) |
|-----------|---------|
| Tetraethylene glycol dimethacrylate | 15.0 |
| Terpolymer of ethyl acrylate/methyl methacrylate/acrylic acid (56/37/7), MW 260,000 | 35.3 |
| Copolymer of styrene/maleic anhydride (58/42), esterified, MW 10,000 | 36.7 |
| 2-(o-Chlorophenyl)-4,5-diphenylimidazolyl dimer | 8.6 |
| Methylene chloride | 527 |
| Methanol | 40 |

To 10 g of this stock solution were added 0.0407 g of 6-nitroveratraldehyde photoinhibitor and 0.0140 g of the sensitizer from Example 1. Portions of this solution were board coated with a 2-mil (51-μm) doctor knife on the resin-subbed side of the oriented polyester film substrate described in Example 6, and the coatings were air-dried. The dried coatings were laminated with a 1-mil (25-μm) oriented polyester film coversheet at 82° at a rate of 4 ft/min (1.22 m/min) at 40 psi (276 kPa).

One half the surface of a photosensitive element was covered by a black polyethylene sheet. A $\sqrt[3]{2}$ step wedge process transparency was placed over the uncovered side and the plate was placed in a vacuum printing frame. An imagewise exposure (positive exposure) was made to radiation from a 2 KW Berkey mercury photopolymer lamp at a distance of 38 in (96 cm) for a time which corresponds to a radiation dosage of 10 units. The polyethylene sheet was removed and a $\sqrt[3]{2}$ step wedge was placed over the previously blocked-off section. A U.V. cut-off filter which absorbed essentially all radiation below about 420 nm was placed over the plate and the entire plate was given a 30 unit exposure. This final exposure gave a negative exposure to the blocked-off section and completed the two-exposure positive sequence on the other half. The exposed element was developed at 22° in a solution prepared from 1536 g of distilled water, 84 g of potassium carbonate·1.5 H$_2$O, and 5 g of potassium hydrogen carbonate, and the developed element was rinsed with a 32° water spray at 40 psi (276 kPa). A development time of 10 seconds gave a positive mode speed of 1, i.e., the first step of the positive image was completely unpolymerized, and a negative mode speed of 10, i.e., the negative image showed 10 full and partial polymerized steps.

EXAMPLES 13 TO 15

Photopolymerizable compositions were prepared, exposed, and developed as described in Example 12 except that the sensitizer from Example 1 was replaced with the sensitizers shown in Table 2 and a development time of 6 seconds was used. The results, summarized in Table 2, show that a good image was obtained in each instance.

TABLE 2

| | | Photopolymerization Speed | |
|---------|-----------------|---------------|---------------|
| Example | Sensitizer, g   | Positive Mode | Negative Mode |
| 13      | Example 2, 0.0151 | 2           | 10            |
| 14      | Example 3, 0.0160 | 6           | 10            |
| 15      | Example 4, 0.0112 | 7           | 5             |

EXAMPLE 16

3-[4-(1-Pyrrolidino)phenyl]-1-(9,10-dihydro-9,10-ethanoanthracen-2-yl)-2-propen-1-one (8)

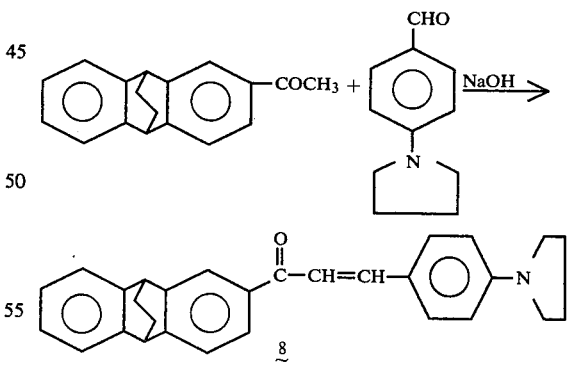

A solution of 3.7 g of 2-acetyl-9,10-dihydro-9,10-ethanoanthracene (15 mmole), 2.6 g of p-(1-pyrrolidino)benzaldehyde (15 mmole), 0.66 g of sodium hydroxide (16.5 mmole) in 100 ml of ethanol was stirred under nitrogen at 40° to 50° for 30 hr. The reaction mixture was allowed to stand an additional 60 hr at 25°. A yellow solid which precipitated was separated from the cooled (ice bath) reaction mixture and washed with cold ethanol to give 4.2 g (69% yield) of the reaction product 8, mp 162° to 164°. λ$_{max}$ (CHCl$_3$): 422 nm ($\epsilon$=31,300), 330 nm (Sh; 4240), 277 nm (22,700). The nmr spectrum was consistent with the assigned structure. Calcd. for $C_{29}H_{27}NO$: C, 85.89; H, 6.71; N, 3.45. Found: C, 85.01, 85.32; H, 6.60, 6.63; N, 3.24, 3.19.

EXAMPLE 17

3-[4-(4-Morpholino)phenyl]-1-(9,10-dihydro-9,10-ethanoanthracen-2-yl)-2-propen-1-one (9)

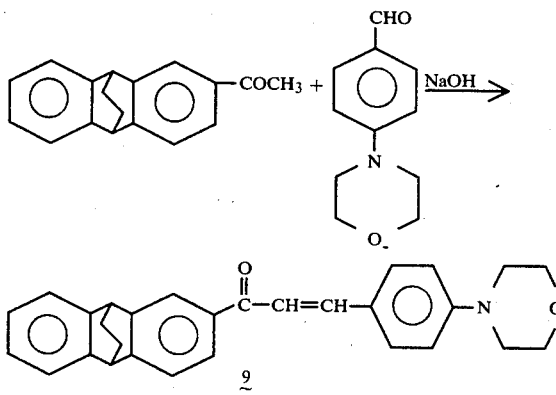

A solution of 3.72 g of 2-acetyl-9,10-dihydro-9,10-ethanoanthracene (15 mmole), 2.87 g of p-(4-morpholino)benzaldehyde) (15 mmole), and 0.66 g of sodium hydroxide (16.5 mmole) in 100 ml of ethanol was stirred under nitrogen at about 50° for 26 hr. The reaction mixture was cooled to 0° and the yellow solid product separated by filtration and washed with cold ethanol to give 4.1 g (65% yield) of the product, 9, mp 142° to 145°. $\lambda_{max}$ (CHCl$_3$): 382 nm ($\epsilon$=21,100), 272 nm (16,400). Calcd. for $C_{29}H_{27}NO_2$: C, 82.63; H, 6.46; N, 3.32. Found: C, 82.60; H, 6.42; N, 3.17.

EXAMPLE 18

3-(1-Ethyl-1,2,3,4-tetrahydroquinol-6-yl)-1-(9,10-dihydro-9,10-ethanoanthracen-2-yl)-2-propen-1-one (10)

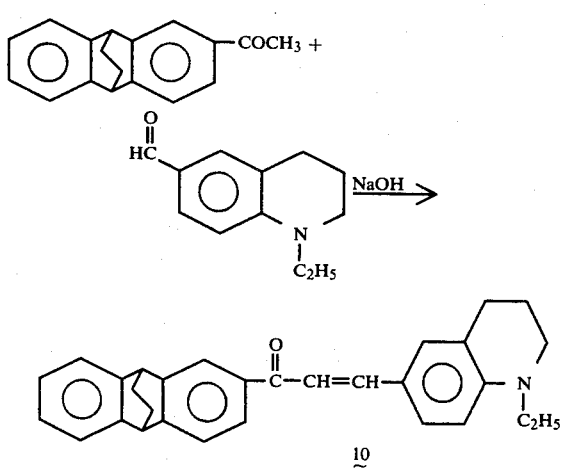

A solution of 3.7 g of 2-acetyl-9,10-dihydro-9,10-ethanoanthracene (15 mmole), 2.8 g of 1-ethyl-1,2,3,4-tetrahydroquinoline-6-carboxaldehyde (15 mmole), and 0.66 g of sodium hydroxide (16.5 mmole) in 90 ml of ethanol was stirred under nitrogen at about 50° for 24 hr. The reaction mixture was poured into a mixture of ether and water, the organic layer was separated, washed with water, an dried over sodium sulfate. Evaporation of the ether left 4.0 g (64% yield) of yellow solid product 10, mp 70° to 72°. The nmr spectrum was consistent with the assigned structure. $\lambda_{max}$ (CHCl$_3$): 433 nm ($\epsilon$=21,500) 356 nm (9490), 272 nm (15,300).

EXAMPLES 19 TO 21

Photopolymerizable compositions were prepared, exposed, and developed as described in Example 12 except that the sensitizer from Example 1 was replaced with the sensitizers shown in Table 3, and a development time of 7 seconds was used. The results, summarized in Table 3, show that a good image was obtained in each instance.

TABLE 3

| Example | Sensitizer, g | Photopolymerization Speed | |
|---|---|---|---|
| | | Positive Mode | Negative Mode |
| 19 | Example 16, 0.0150 | 1 | 10 |
| 20 | Example 17, 0.0156 | 4 7 | |
| 21 | Example 18, 0.0155 | 6 | 11 9 |

I claim: The embodiments of the invention in which an exclusive property or privilege is claimed are defined as follows:

1. A composition having the formula

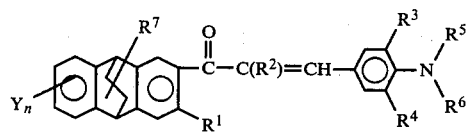

wherein:

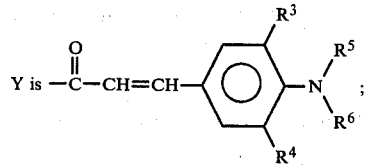

$R^1$ and $R^2$ are each H, or, $R^1 + R^2$ is —CH$_2$—;
$R^3$ is H, or $R^3 + R^5$ is selected from —CH$_2$CH$_2$— and —CH$_2$CH$_2$CH$_2$—;
$R^4$ is H, or, $R^4 + R^6$ is selected from —CH$_2$CH$_2$— and —CH$_2$CH$_2$CH$_2$—;
$R^5$ and $R^6$ are alkyl groups of 1 to 5 carbon atoms, or together are selected from —(—CH$_2$—)$_4$ and —CH$_2$CH$_2$OCH$_2$CH$_2$—;
$R^7$ is H or CH$_3$; and
n is 0 or 1, with the proviso that when n is 1, $R^1$ and $R^2$ are H.

2. A composition according to claim 1 wherein $R^1$, $R^2$ and $R^7$ are H and n=0.

3. A composition according to claim 2:

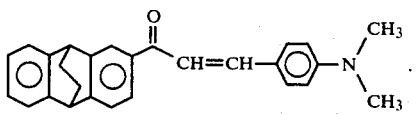

4. A composition according to claim 2:

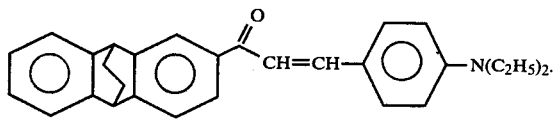

5. A composition according to claim 2:

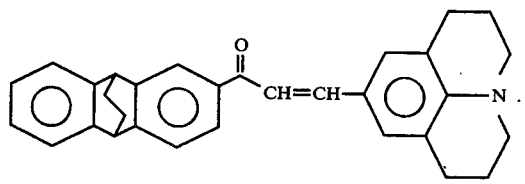

6. A composition according to claim 2:

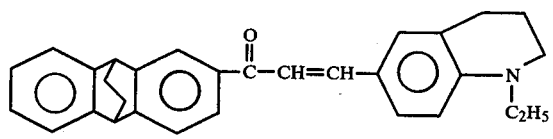

7. A composition according to claim 1 wherein $R^1$, $R^2$, $R^3$, $R^4$ and $R^7$ are H, and $R^5$ and $R^6$ are each $CH_3$ or $C_2H_5$.

8. A composition according to claim 7:

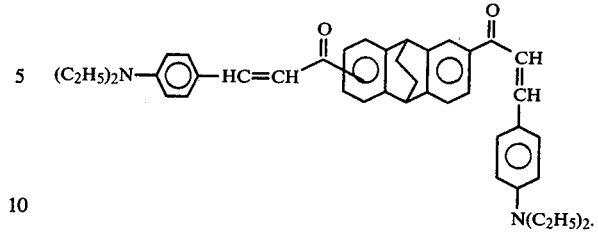

9. A composition according to claim 7:

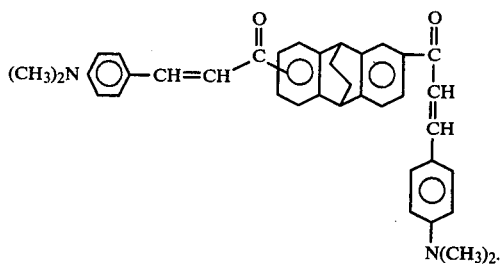

10. A composition according to claim 1 wherein $R^1$, $R^2$, $R^3$, $R^4$ and $R^7$ are H, and $R^5 + R^6$ is selected from $(CH_2)_4$ and $(CH_2)_2 O (CH_2)_2$.

11. A composition according to claim 10:

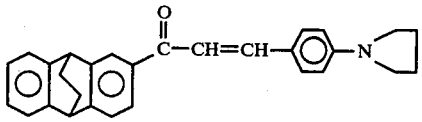

12. A composition according to claim 10:

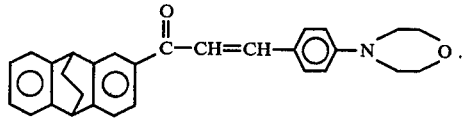

* * * * *